US010952988B2

(12) United States Patent
Varloud et al.

(10) Patent No.: US 10,952,988 B2
(45) Date of Patent: Mar. 23, 2021

(54) METHODS FOR CONTROLLING THE SPREAD OF DIROFILARIOSIS

(71) Applicant: Ceva Santé Animale, Libourne (FR)

(72) Inventors: Marie Varloud, Libourne (FR); Elizabeth Hodgkins, Yorba Linda, CA (US)

(73) Assignee: Ceva Santé Animale, Libourne (FR)

( * ) Notice: Subject to any disclaimer, the term of this patent is extended or adjusted under 35 U.S.C. 154(b) by 0 days.

(21) Appl. No.: 15/743,179

(22) PCT Filed: Jul. 8, 2016

(86) PCT No.: PCT/EP2016/066247
§ 371 (c)(1),
(2) Date: Jan. 9, 2018

(87) PCT Pub. No.: WO2017/009219
PCT Pub. Date: Jan. 19, 2017

(65) Prior Publication Data
US 2018/0235926 A1 Aug. 23, 2018

(30) Foreign Application Priority Data

Jul. 10, 2015 (EP) .................................... 15306145

(51) Int. Cl.
| | |
|---|---|
| *A61K 31/341* | (2006.01) |
| *A61K 45/06* | (2006.01) |
| *A61K 31/4402* | (2006.01) |
| *A61K 31/215* | (2006.01) |
| *A01N 51/00* | (2006.01) |
| *A61K 31/34* | (2006.01) |
| *A01N 53/00* | (2006.01) |
| *A61P 33/10* | (2006.01) |
| *A61K 9/00* | (2006.01) |
| *A61K 31/216* | (2006.01) |
| *A61K 31/351* | (2006.01) |

(52) U.S. Cl.
CPC ............ *A61K 31/341* (2013.01); *A01N 51/00* (2013.01); *A01N 53/00* (2013.01); *A61K 9/0017* (2013.01); *A61K 31/215* (2013.01); *A61K 31/216* (2013.01); *A61K 31/34* (2013.01); *A61K 31/4402* (2013.01); *A61K 45/06* (2013.01); *A61P 33/10* (2018.01); *A61K 31/351* (2013.01); *A61K 2300/00* (2013.01)

(58) Field of Classification Search
CPC .. A61K 31/341; A61K 45/06; A61K 31/4402; A61K 31/215; A61K 31/34; A61K 9/0017; A61K 31/216; A61K 31/351; A61K 2300/00; A01N 51/00; A61P 33/10
See application file for complete search history.

(56) References Cited

U.S. PATENT DOCUMENTS

| | | | |
|---|---|---|---|
| 7,368,435 B2 | 5/2008 | Cottrell et al. | |
| 2008/0194642 A1 | 8/2008 | Albright et al. | |
| 2011/0092560 A1 | 4/2011 | del Bigio | |
| 2012/0255502 A1 | 10/2012 | Holmes | |
| 2013/0225516 A1 | 8/2013 | Soll et al. | |
| 2018/0213790 A1 | 8/2018 | Karembe et al. | |
| 2020/0163339 A1 | 5/2020 | Karembe et al. | |

FOREIGN PATENT DOCUMENTS

| | | | |
|---|---|---|---|
| EP | 0 295 117 A1 | 12/1988 | |
| EP | 0 649 845 A1 | 4/1995 | |
| WO | WO 2005/015995 A1 | 2/2005 | |
| WO | WO-2006039079 A2 * | 4/2006 | ............. A01N 43/90 |
| WO | WO 2007/143298 A2 | 12/2007 | |
| WO | WO 2009/027506 A2 | 3/2009 | |
| WO | WO 2010/109214 A2 | 9/2010 | |
| WO | WO 2012/107585 A1 | 8/2012 | |
| WO | WO 2013/152315 A1 | 10/2013 | |

OTHER PUBLICATIONS

SVP7 EPA Label Amendment, Registration No. 83399-6 (Year: 2014).*
Heather Hoch & Keith Strickland, Canine and Feline Dirofilariasis: Prophylaxis, Treatment, and Complications of Treatment, Compendium: Continuing Education for Veterinarians, Mar. 2008, p. 146 (Year: 2008).*
Heather Hoch & Keith Strickland, Canine and Feline Dirofilariasis: Life Cycle, Pathophysiology, and Diagnosis, Compendium: Continuing Education for Veterinarians, Mar. 2008, p. 133 (Year: 2008).*
John. W. McCall, The Safety-Net Story About Macrocyclic Lactone Heartworm Preventives: A Review, an Update, and Recommendations, 133 Vet. Parasitol. 197 (Year: 2005).*
Catherine Bourguinat, et al, Macrocyclic Lactone Resistance in Dirofilaria immitis, 181 Vet. Parasitol. 388 (Year: 2011).*
International Search Report and Written Opinion for Application No. PCT/EP2016/066247 dated Sep. 22, 2016.
International Preliminary Report on Patentability for Application No. PCT/EP2016/066247 dated Jan. 25, 2018.
[No Author Listed], Vectra 3D: Annex I Summary of Product Characteristics. Jan. 1, 2013. Last accessed from http://ec.europa.eu/health/documents/community-register/2013/20131204127161/anx_127161_en.pdf on Sep. 15, 2016. 25 pages.
Leonardi, Vectra 3D for dogs—Flea Med Precautions and Use. Sep. 25, 2013. Last accessed from https://www.petcarerx.com/article/vectra-3d-for-dogs-flea-med-precautions-and-use/1366 on Dec. 3, 2015. 8 pages.

(Continued)

*Primary Examiner* — Sean M Basquill
(74) *Attorney, Agent, or Firm* — Wolf, Greenfield & Sacks, P.C.

(57) ABSTRACT

This invention relates to a method of controlling the spread of dirofilariosis, such as for example heartworm, by administering to at least one non-human animal infested with filarioid nematodes such as *Dirofilaria* spp or susceptible to have been infested with filarioid nematodes such as *Dirofilaria* spp, an effective dose of a combination of a neonicotinoid compound and a pyrethroid compound.

16 Claims, No Drawings

(56) References Cited

OTHER PUBLICATIONS

Testa et al., Predicting drug metabolism: Concepts and challenges. Pure Appl. Chem. 2004;76(5):907-914.
U.S. Appl. No. 15/747,374, filed Jan. 24, 2018, Karembe et al.
PCT/EP2016/066247, dated Sep. 22, 2016, International Search Report and Written Opinion.
PCT/EP2016/066247, dated Jan. 25, 2018, International Preliminary Report on Patentability.
Diaz, Introduction to ectoparasitic diseases. Principles and Practice of Infectious Diseases. 2015;8:1 page.
U.S. Appl. No. 16/776,303, filed Jan. 29, 2020, Karembe et al.

\* cited by examiner

METHODS FOR CONTROLLING THE SPREAD OF DIROFILARIOSIS

RELATED APPLICATIONS

This application is a national stage filing under 35 U.S.C. § 371 of International Application No. PCT/EP2016/066247, entitled "Combinations of a Neonicotinoid and a Pyrethroid for Controlling the Spread of Dirofilariosis," which has an international filing date of Jul 8, 2016, which claims foreign priority benefits under 35 U.S.C. § 119(a)-(d) or 35 U.S.C. § 365(b) of European Application No. EP 15306145.2, filed Jul. 10, 2015, the entire disclosure of each of which is herein incorporated by reference in its entirety.

FIELD OF THE INVENTION

This invention relates to a method for controlling the spread of dirofilariosis disease, generally due to *Dirofilaria immitis* and/or *Dirofilaria. repens*, by administering to a dog infected by *Dirofilaria.* an effective dose of a combination of a neonicotinoid compound and a pyrethroid compound.

BACKGROUND

Dirofilariosis are widespread diseases caused by filarioid nematodes (superfamily Filarioidea) of the genus *Dirofilaria* (*Dirofilaria* spp) that spread from host to host through the bites of mosquitoes. The principal agent of canine dirofilariosis in the Americas is *Dirofilaria immitis* but it can also infect cats, wolves, coyotes, foxes and other animals, such as ferrets, sea lions and even bovines, equine and humans. The parasite is commonly called "heartworm" because the adult reproductive stage of its life cycle resides primarily close to the heart, in the pulmonary artery of dogs where it can live for many years. Heartworm infection will result in serious disease and possible death for the host. When a mosquito bites an infected and microfilaremic animal, young heartworms called microfilariae enter into the mosquito's digestive system. Within two weeks, the microfilariae develop into infective larvae inside mosquitoes and migrate up to the proboscis; these infective larvae can be transmitted to another animal when mosquitoes take their next blood meals. Upon entering the dogs, the larvae develop and migrate to the dog's heart where they mature and breed. Development of the larvae into adult worms takes about 180 days in dogs. When at least one male and one female adult worms have developed, they can produce offspring called microfilariae. These microfilariae are released in the bloodstream of the host from where they can be ingested by a mosquito that feeds upon the infected hosts. The *Dirofilaria. immitis* life cycle is completed when the ingested microfilariae mature into infective larvae in the mosquito. Once mature, heartworms can live for 5 to 7 years in dogs and up to 2 or 3 years in cats. Because of the longevity of these worms, each mosquito season can lead to an increasing number of worms in an infected pet.

*Dirofilaria. immitis* presents as white threadlike round worms reaching up to 20 cm for adult males (12-20 cm) and 31 cm for adult females (25-31 cm), with a mean diameter of 1 mm. They are characterized by a relatively smooth cuticle. Heartworms are primarily found in the pulmonary artery in dogs with low parasitic burden (<50 worms). In infestations with high parasitic burden (>50 worms), they may reach the right ventricle, right atrium, and occasionally vena cava. The initial response includes swelling of small pulmonary arteries and blood clotting. The physical presence of the heartworm parasite in the pulmonary artery and right ventricle of the canine heart, and the resulting destruction of tissue, causes respiratory and circulatory problems which can be fatal under conditions of stress or vigorous exercise. Pulmonary hypertension and right-sided congestive heart failure may result. Because it takes a large number of heartworms to clog up blood flow to a significant degree, heartworms can be present inside the heart for up to 2 or 3 years before causing clinical signs. As the disease progresses, lung tissue can be destroyed leading to a worsening cough and liver and kidney damage can occur due to reduced blood flow to these organs. If left untreated, heartworm disease may result in death. After adult heartworms mate and produce immature heartworms, an infected dog which is bitten by an uninfected mosquito will transmit microfilariae to the mosquito, beginning the cycle again. The life cycle of the heartworm is approximately 6 months. The heartworm parasite has also been shown to be zoonotic and causing focal lung, liver, eye and cutaneous lesions in man (Hamilton, R. G., et al, Exper. Parasitol., 56:298-313 (1983)).

Dirofilariosis and for example heartworm disease is present all over the world and may be also spreading to new regions of the world, notably because of traveling pets and invasive vectors. Stray and neglected dogs and certain wildlife such as coyotes, wolves, and foxes can also be carriers of heartworms. Mosquitoes blown great distances by the wind and the relocation of infected pets to previously uninfected areas also contribute to the spread of heartworm disease.

Heartworm disease due to *Dirofilaria immitis* continues to cause severe disease and even death in dogs and other animals (cats, bovines, humans, guinea porcine, and ferrets) in many parts of the world, even though safe, highly effective and convenient preventatives have been available for the past two decades. Moreover, the parasite and vector mosquitoes continue to spread into areas where they have not been reported previously. The control of such parasites has long been recognized as an important aspect of human and animal health regimens. Although a number of alternatives to control infestation are in use, these suffer from a variety of problems, including a limited spectrum of activity, the need for repeated treatment (lack of compliance) and, now emerging, resistance by parasites.

Currently for curative treatment, only heart surgery and two arsenic derivatives are available for clinically infested dogs, namely thiacetarsamide (Caparsolate® marketed by Abbott laboratories) and melarsomine dihydrochloride (Immiticide® marketed by Merial). The treatment is expensive, integrated in a complex protocol during which the life of the treated animal is at risk. The protocol requires that the activity of the animal is reduced to a strict minimum. The sudden death of the worms may cause a fatal shock to the animal.

For chemoprophylaxis, two alternatives are possible to prevent heartworm disease in dogs: daily administration of diethylcarhamazine citrate, or monthly administration of macrocyclic lactones.

Number of macrocyclic lactones have been commercialized, as sole active ingredient, such as for example ivermectin (Heartgard® marketed by Merial), doramectin (Dectomax® marketed by Zoetis), moxidectin or abamectin (Avomec® marketed by Merial), milbemycin oxime (Interceptor®, marketed by Elanco) or Selamectin (Revolution® marketed by Zoetis), and some in combination with another active compound, such as for example milbemycin oxime and lufenuron and/or praziquantel (Sentinel® and Sentinel® Spectrum marketed by Virbac), mylbemicin oxime and spinosad (Trifexis® marketed by Elanco), imidaclorpid and moxidectin (Advantage® Multi marketed by Bayer Animal Health), ivermectin and pyrantel pamoate and/or praziquantel (Tri heart marketed by Merck or Iverhart® max marketed by Virbac).

Also, a slow release formulation of subcutaneously injected moxidectin-impregnated lipid microspheres, providing single dose continuous protection in excess of six months, has been marketed by Fort Dodge under the name of Moxidectin SR®, ProHeart 6® or Guardian SR®. However, this product was voluntarily removed from the US market in September 2004 for issues related to safety, and currently has been allowed once again by FDA under a risk minimization and restricted distribution program.

Further the currently marketed ivermectin formulations come with certain precautions for usage. The American Heartworm Society (AHS) recognizes the safety-net (or reach-back effect) and adulticidal properties of some macrocyclic lactones, particularly ivermectin. However, heartworm-positive working dogs might be more at risk to develop severe thromboembolism and death. Worsened radiographic and echocardiographic images with greatly restricted exercise suggest that such treatment is contraindicated. Furthermore, the use of macrocyclic lactones is contraindicated in heartworm positive dogs since this can contribute to select resistant strains of nematodes and because it can be dangerous to the treated animal. That is the reason why, in asymtomatic dogs, macrocylic lactones should be administered with much caution and with regular testing and clinical examination by a veterinarian at least once every 4-6 months. Likewise, ivermectin must be used with caution in collies and related shepherd dogs that are more susceptible to its neurotoxic effects than other dog breeds.

Accordingly, there is a need for a product which could control the spread of heartworm infestation, notably in order to overcome the foregoing problems.

It has been found surprisingly that administration of a combination of a neonicotinoid compound and a pyrethroid compound to an animal prevents the spread of filarioid nematodes such as *Dirofilaria* spp. to other animals, notably by inhibiting feeding and killing the mosquito vectors exposed to animals with filarioid nematodes.

SUMMARY OF THE INVENTION

The present invention provides herein a method of controlling the spread of dirofilariosis, such as for example heartworm disease, by administering or applying to at least one non-human animal infested with filarioid nematodes, such as *Dirofilaria* spp, or susceptible to have been infested with filarioid nematodes, such as *Dirofilaria* spp, an effective dose of a combination of a neonicotinoid compound and a pyrethroid compound.

The invention also provides a method of controlling the spread of dirofilariosis, such as for example heartworm disease, in a group of non-human animals, by administering or applying to at least one non-human animal infested with filarioid nematodes, such as *Dirofilaria* spp, or susceptible to have been infested with filarioid nematodes, such as *Dirofilaria* spp, among the group an effective dose of a combination of a neonicotinoid compound and a pyrethroid compound.

The present invention still further provides a kit suitable for implementing a method for controlling the spread of dirofilariosis as defined herein. Said kit comprises one or several packaging units, said packaging units comprising a combination of a neonicotinoid compound and a pyrethroid compound, and preferably a leaflet giving instructions for administering or applying said combination to a non-human animal infested or susceptible to have been infested with filarioid nematodes, such as *Dirofilaria* spp, or susceptible to have been infested with filarioid nematodes, such as *Dirofilaria* spp.

DETAILED DESCRIPTION

"Animals" or "animal subject" or "subject" refers to any non-human animals able to develop dirofilariosis. The subject may be any canidae, such as dog, fox, coyote, or wolf, felidae, such as cat, lion, or panther, bovidae, such as cattle or dairy cow, equidae, such as horse, or camelidae, such as camel. According to particular embodiments, the animals are canidae or felidae, and preferably dogs or cats. In a specific embodiment, the animal is a dog.

"Dirofilariosis" as used herein includes diseases caused by filarioid nematodes (superfamily Filarioidea) of the genus *Dirofilaria*, which are transmitted by a plethora of mosquito species. The principal *Dirofilaria* agents (*Dirofilaria* spp) include *Dirofilaria immitis* and *Dirofilaria repens*. Dirofilariosis may be illustrated for example by heartworms diseases and/or infestation which are generally due to roundworms that typically reside within the heart of a host during the final reproductive stages of its life cycle.

"Combination" as used herein may broadly include two or more elements or compounds physically, chemically, and/or otherwise suitably coupled with each other to produce a desired result. Both components of the combination may be administered or applied simultaneously or sequentially and may be separate dosage forms or may be part of same dosage form.

"Controlling" as used herein may broadly include the reduction, the eradication and/or the prevention of the spread of dirofilariosis.

"Spread of dirofilariasis" as used herein means propagation of dirofilariosis. More specifically, the method allows not to propagate dirofilariasis by mosquitoes (especially non-infested mosquitos) in contact with non-human animals infested or susceptible to have been infested with filarioid nematodes (i.e., non-human animals having microfilaria that circulate in the bloodstream or microfilaremic non-human animals) to non-human animals which are not infested with filarioid nematodes yet. As it is illustrated by the examples, the composition of the invention is effective in inhibiting the uptake of microfilaria by mosquitoes from microfilaremic non-human animals.

Neonicotinoid compounds are a class of neuro-active insecticides chemically similar to nicotine. They exhibit an agonist activity for the nicotinic acetylcholine receptors agonists and cause a strong stimulation of nerve cells involving paralysis and death of the parasite with affecting the host animal receptors making them relatively innocuous to the mammals and humans. They have been introduced on market in the 90's and are particularly active against ectoparasites such as fleas, flies and lice. Typical neonicotinoid compounds include without limitation imidacloprid, thiamethoxam, clothianidin, acetamiprid, thiacloprid, dinotefuran, nitenpyram, imidaclothiz, huanyanglin, guadipyr, paichongding, cycloxaprid and metabolites, derivatives or salts thereof.

A preferred neonicotinoid compound of the invention is dinotefuran and the derivatives, metabolites or salts thereof.

As used in the present description, the term "dinotefuran" can also comprises its derivatives or analogs, metabolites, and salts.

Dinotefuran has been described by the company Mitsui Toatsu Chemicals, Inc. in EP 0 649 845 and has been developed for controlling insect pests. Dinotefuran, also called 2-methyl-1-nitro-3-[(tetrahydro-3-furanyl) methyl] guanidine, has the following formula:

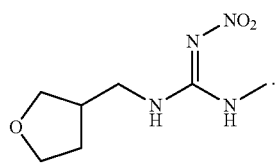

Neonicotinoids and especially dinotefuran are subjected to metabolism in non-human mammals and as a result, metabolites may induce a long-lasting action of neonicotinoids against ectoparasites. The principal metabolic pathways of dinotefuran in mammals involve N-demethylation, nitro reduction, and N-methylene hydroxylation accompanied by amine cleavage. The metabolites of dinotefuran comprise the compounds as disclosed by Simon-Delso et al. (*Systemic insecticides (neonicotinoids and fipronil): trends, uses, mode of action and metabolites*, Environ. Sci. Pollut. Res., 2015, 22:5-34) and by Ford K A and Casida J E (Unique and common metabolites of thiamethoxam, clothianidin, and dinotefuran in mice, Chem. Res. Toxicol., 2006, 19:1549-1556; Neonicotinoid metabolism: compounds, substituents, pathways, enzymes, organisms, and relevance, J. Agric. Food Chem., 2011, 59:2923-2931) and FAO dinotefuran (http://www.fao.org/fileadmin/templates/agphome/documents/PestsPesticides/JMPR/Evaluation12/Dinotefuran.pdf). Typically, the metabolite of dinotefuran comprise, without limitation, N-desmethyl dinotefuran (2-nitro-1-(tetrahydro-3-furylmethyl)guanidine), DIN-NNO, DIN-dm-NNO, DIN-NNH2, 1-methyl-3-(tetrahydro-3-furylmethyl)guanidine, 3-(tetrahydro-3-furylmethyl)guanidine, 1-methyl-3-(tetrahydro-3-furylmethyl)urea, 3-(tetrahydro-3-furylmethyl)urea, 2-hydroxy-dinotefuran, 4-hydrox-dinotefuran, 1,3-diazinane aminocarbinol, DIN-b (derivative of DIN-dm), DIN-e (guanidine derivative of DIN-a), DIN-f (guanidine derivative of DIN-b), DIN-g (derivative of DIN-5-OH), DIN-h (desmethyl-g), DIN-I (nitroso derivative of DIN-g), DIN-j (nitrosoderivative of DIN-h), DIN-k (guanidine derivative of DIN-h), tetrahydrofuran carboxaldehyde (3-furfural), tetrahydrofuran alcohol (3-furfuryl alcohol), tetrahydrofuran-3carboxylic acid, 4-hydroxy-tetrahydrofuran-3-carboxylic acid, tetrahydrofuran-3-yl-methylamine, 1-[4-hydroxy-2-(hydroxymethyl)butyl]-3-methyl-2-nitroguanidine, and 3-hydroxy dinotefuran.

Typically, the derivatives or analogs of dinotefuran comprise all the compounds as disclosed in the EP 0 649 845 patent. More particularly, the derivatives or analogs of dinotefuran comprise, without limitation, 1-[{(tetrahydro-3-furanyl)methyl} amino]-1-methylamino-2-nitroethylene, 1-[{(tetrahydro-3-furanyl)methyl} amino]-1-ethylamino-2-nitroethylene, 1-[{(tetrahydro-3-furanyl)methyl} amino]-1-dimethylamino-2-nitroethylene, 1-[{(tetrahydro-3-furanyl)methyl} amino]-1-(1-pyrrolidinyl)-2-nitroethylene, 1-[N-{(tetrahydro-3-furanyl)methyl}-N-methylamino]-1-methylamino-2-nitroethylene, 1-[N-{(tetrahydro-3-furanyl)methyl}-N-propylamino]-1-methylamino-2-nitroethylene, 1-[N-{(tetrahydro-3-furanyl)methyl}-N-propylamino]-1-ethylamino-2-nitroethylene, 1-{(tetrahydro-3-furanyl)methyl}-2-nitro-3-methylguanidine, N-{(tetrahydro-3-furanyl)-methyl}-N-(methyl)nitroguanidine, 1-{(tetrahydro-3-furanyl)methyl}-1-ethyl-2-nitro-3-methylguanidine, N-(tetrahydro-3-furanyl)-methyl-N'-cyano(methylthio)formamidine, N-cyano-N'-{(tetrahydro-3-furanyl)methyl} acetamidine, N-cyano-N'-{(tetrahydro-3-furanyl)methyl}-N-methylacetamidine, N-[4-{(2-methyl) tetrahydrofuranyl}methyl]-N'-methyl-N"-nitroguanidine, 1-{(tetrahydro-3-furanyl)methyl}-1,2-dicyclohexylcarbonyl-2-methyl-3-nitroguanidine, 1-{(tetrahydro-3-furanyl) methyl}-1,2-diethylcarbonyl-2-methyl-3-nitroguanidine, 1-{(tetrahydro-3-furanyl)methyl}-1,2-dimethoxycarbonyl-2-methyl-3-nitroguanidine, and 1-{(tetrahydro-3-furanyl) methyl}-1,2-dibenzoyl-2-methyl-3-nitroguanidine.

Pyrethroid compounds are a class of compounds acting on the nervous system of insects, and disrupt the function of the neurons by interacting with sodium channels. Examples of pyrethroid include one or more of etofenprox, permethrin, prallethrin, resmethrin, sumithrin, allethrin, alpha-cypermethrin, bifenthrin, beta-cypermethrin, cyfluthrin, cypermethrin, deltamethrin, flumethrin, esfenvalerate, lamdba-cyhalothrin, or zeta-cypermethrin. According to a particular embodiment, the pyrethroid compound is permethrin.

In a preferred embodiment, the current invention provides a method of controlling the spread of dirofilariosis, such as for example heartworm disease, by administering to at least one non-human animal infested with filarioid nematodes, such as *Dirofilaria* spp, or susceptible to have been infested with filarioid nematodes such as *Dirofilaria* spp, an effective dose of a combination of a neonicotinoid compound and a pyrethroid compound sufficient for mosquitos' repellency and/or for killing mosquitos, where the weight ratio of pyrethroid compound to neonicotinoid compound ranges from 4-15, preferably from 6 to 9, and more preferably from 7-8.

The non-human animals infested with filarioid nematodes, such as *Dirofilaria* spp, or susceptible to have been infested with filarioid nematodes, such as *Dirofilaria* spp, are more specifically non-human animals having microfilaria that circulate in the bloodstream. The microfilaremic non-human animals can be symptomatic but more often asymptomatic. There are few, if any, early signs of disease when a non-human animal is infected with filarioid nematodes, so detecting their presence with a filarioid nematodes test can be important. The filarioid nematodes test can be a test assessing the presence or not of microfilariae. The test usually requires a blood sample from the non-human animal, wherein the presence or absence of filarioid nematodes proteins is assessed by an antigen test. Once said test is positive, the animal is generally called a microfilaremic animal. Once an animal is positive on an antigen test, the diagnosis is preferably confirmed with an additional and generally different test. Microfilaremia can be assessed using a different blood test (Knott modified).

According to an embodiment, the invention provides a method of controlling the spread of dirofilariosis, such as heartworm disease, by administering or applying to at least one non-human animal diagnosed as infected with filarioid nematodes, such as *Dirofilaria* spp, an effective dose of a combination of a neonicotinoid compound and a pyrethroid, and optionally a macrocyclic lactone.

According to an embodiment, the invention provides a method of controlling the spread of dirofilariosis, such as heartworm disease, by detecting the presence of microfilaria, more specifically microfilaria proteins, in a non-human animal, more specifically from a blood sample from a non-human animal, and then administering or applying to the non-human animal diagnosed as infected with filarioid nematodes an effective dose of a combination of a neonicotinoid compound and a pyrethroid compound, and optionally a macrocyclic lactone.

As mentioned before, the method of the present invention can be implemented on a group of non-human animals (for instance 2, 3, 4, 5, etc., up to 20, 50, 100, 200 animals). In that context, and according to a particular embodiment, the invention provides a method of controlling the spread of dirofilariosis, such as for example heartworm disease, in a group of non-human animals, wherein the method comprises administering or applying an effective dose of a combination of a neonicotinoid compound and a pyrethroid, with optionally a macrocylcic lactone, to at least one animal diagnosed as infected with filarioid nematodes in said group of animals. The method is particularly useful in farms/houses where several non-human animals are kept and/or raised, such as kennels. According to a particular embodiment, the said at least non-human animal is or lives among a group of non-human animals, which allows thereby to control the spread of dirofilariasis among said group.

According to another embodiment, the invention provides a method of controlling the spread of dirofilariosis, such as heartworm disease, in a group of non-human animals, by detecting the presence of microfilaria, more specifically microfilaria proteins, in a group of animals, and then administering or applying an effective dose of a combination of a neonicotinoid compound and a pyrethroid compound, and optionally a macrocyclic lactone, to at least one non-human animal diagnosed as infected with filarioid nematodes within said group.

More specifically, the presence of microfilaria is assessed from a blood sample of a non-human animal.

The method of the invention allows therefore inhibiting the transmission of filarioid nematodes, such as *Dirofilaria* spp, to the non-infected non-human animals within said group of animals.

The present invention also provides herein a combination of a neonicotinoid compound and a pyrethroid compound for use in a method of controlling the spread of dirofilariosis, such as for example heartworm disease. More specifically, the combination as defined herein is administered to at least one non-human animal infested with filarioid nematodes, such as *Dirofilaria* spp, or susceptible to have been infested with filarioid nematodes, such as *Dirofilaria* spp.

In yet another preferred embodiment of the invention, the combination of a neonicotinoid compound and a pyrethroid compound, as defined above, further comprises an insect growth regulator (IGR). Preferably, the IGR is pyriproxyfen or methoprene. According to specific embodiment the IGR is pyriproxyfen.

Preferably, the insect growth regulator is packaged in the same chamber as either the neonicotinoid compound or the pyrethroid compound or in yet another container.

According to specific embodiments, the weight ratio of IGR to neonicotinoid compound ranges from 0.05-0.12, preferably from 0.06 to 0.1, and more preferably from 0.07-0.09.

The effective dose of a combination of a neonicotinoid compound and a pyrethroid compound, and optionally a IGR, is the dose sufficient for mosquitos' repellency and/or for killing mosquitos. More specifically, said dose allows inhibiting feeding and killing mosquitoes exposed to animal with filarioid nematodes, such as *Dirofilaria* spp.

According to an embodiment, the dose is such that it allows an effective effect for up to 15 days, or up to four or eight weeks post-administration. More preferably, the amount of the combination of a neonicotinoid compound and a pyrethroid compound, and optionally a IGR, to be administered is an amount to preferably achieve at least a 80% kill rate of mosquitos, preferably at least a 90%, even more preferably 95%, kill rate of mosquitos.

The mosquitoes, vectors of *Dirofilaria* spp, are generally *Culex pipiens* or *Aedes aegypti*.

The dose may vary in a large range and depends on the animal's body weight. The content of one full combination of a neonicotinoid compound and a pyrethroid compound, and optionally a IGR, (e.g. via an applicator) is preferably applied directly to the animal's skin, preferably after parting its fur, either in one or more spots on the back, depending on the animal's weight, or in a continuous line along the centre of the back from the base of the tail to the shoulder blades. Treatment can be repeated once or twice a month, once every two months or once every three months.

The combination of the invention can be available in compositions, such as solutions or emulsions or gels, where each compound (i.e., neonicotinoid compound and a pyrethroid compound, and optionally IGR, as detailed herein) is in separate compositions or two or three of the compounds are in the same compositions. They can be available for a topical administration such as spot-on or line on solution in one or more containers, more preferably applicators can be available with one or more (2, 3, 4, 5 or 6) different strengths for use on animals of different weights.

Preferably, the formulation comprising the combination of the invention is non-toxic and does not irritate the animal's skin. Applications are typically in the range of 0.5 to 10 mL for canidae and felidae. In certain embodiments of the invention, the compositions are applied in the range of about 0.05 to 0.6 mL/kg of animal's body weight.

In one preferred embodiment of the invention, the composition or combination comprises permethrin in a concentration range of about 60 to 95%, dinotefuran in a concentration range of about 6 to 22%, and pyriproxyfen in a concentration range of about 0.8 to 4%. In another preferred embodiment of the invention, the combination comprises permethrin in a concentration range of about 70 to 90%, dinotefuran in a concentration range of about 8 to 15%, and pyriproxyfen in a concentration range of about 0.9 to 1.5%. All percentages, unless otherwise specified, are on a weight basis and calculated with respect to the total weight of the named compounds.

The administration of the composition or combination of the invention can be oral, topical to the skin or fur, or by injection. Said administration is preferably an application to the non-human animal and more preferably the composition or combination of the invention is applied to the fur or skin of the non-human mammal.

In a further aspect of the invention, the method can further comprise an administration of a macrocyclic lactone to the non-human animal. As mentioned before, the macrocyclic lactones are used to treat dirofilariosis, such as for example heartworm disease in non-human animals. More specifically, macrocyclic lactones are used for a preventive treatment of dirofilariosis. They are usually administered to asymtomatic and microfilaremic non-human animals, especially dogs.

Accordingly, the present invention also provides herein a combination of a neonicotinoid compound and a pyrethroid compound, and at least one macrocyclic lactone, for use in a method of controlling the spread of dirofilariosis, such as for example heartworm disease, among non-human animals. More specifically, the combination as defined herein is administered to at least one non-human animal infested with filarioid nematodes, such as *Dirofilaria* spp, or susceptible to have been infested with filarioid nematodes, such as *Dirofilaria* spp, more particularly said animal is an asymtomatic and microfilaremic non-human animal.

The macrocyclic lactones can include the macrocyclic lactones as identified above. More particularly, the macrocyclic lactone can be ivermectin, doramectin, moxidectin, abamectin, selacmectin, or more preferably milbemycin oxime.

Said administration of a macrocyclic lactone is preferably a simultaneous, separate or sequential administration to the administration of the combination as defined herein. According to a preferred embodiment, the macrocyclic lactone is preferably a concomitant administration to the administration of the combination as defined herein According to a preferred embodiment, said administration is a monthly administration and more preferably is administered simultaneously to the administrations of the combination as defined herein.

The administration of a macrocyclic lactone can be oral, topical to the skin or fur, or by injection. Said administration is preferably an intradermic and/or subcutaneous application. It can be chewable tablets, spots on which are administered monthly, injectable suspensions, or implant formulations.

The macrocyclic lactone is usually administered to the non-human animal after the diagnostic of the presence of filarioid nematodes such as *Dirofilaria* spp, specifically in the blood of said animal.

In a further aspect of the invention, the combination, the compositions or the containers as defined herein, and optionally the macrocyclic lactone, are for use in a method of controlling the spread of dirofilariosis, such as for example heartworm disease, as detailed herein.

In an embodiment of the invention, the combination is packaged in a container, encompassing two associated, preferably attached but individual chambers, which are separated by a barrier, preferably plastic, plastic coated paper or metal, such as aluminum foil. In one embodiment of the invention, the first chamber and the second chamber are plastic tubes that are separate but fused together. During packaging, the first insecticide (i.e., the pyrethroid compound), preferably permethrin, is placed in the first chamber and the second insecticide (i.e., the neonicotinoid compound), preferably dinotefuran, is placed in the second chamber. Preferably, the first and second chambers are separated by a barrier that can prevent any interaction of the first and second insecticides. In another preferred embodiment of the invention, an insect growth regulator, preferably pyriproxyfen, is added to the insecticide composition and placed in the same chamber with either the first insecticide or the second insecticide or even separately in yet another container.

The entire container containing the active compounds in separate chambers is sealed, preferably with a tab or top, for use in opening the container prior to administration. After the container is sealed, the formulation can be safely stored in the container until administration of the insecticide formulation to the animal.

Prior to administration of the combination to the animal, the container is opened by removing the tab or top. In one embodiment of the invention, the container is opened by twisting the tab thereby resulting in breaking or tearing of the barrier separating the two chambers, thereby allowing the two insecticides, preferably permethrin and dinotefuran, to mix prior to administration of the combination to the animal. After the two compounds are mixed, the two compounds are dispensed simultaneously by squeezing or collapsing the body of the individual containers. In another embodiment of the invention, the two are not combined until they are dispensed onto the animal A dual plunger system can also be employed to administer the formulation to the animal.

In another embodiment of the invention, opening of the dual-chamber container does not result in the mixing of the two insecticides. After the container is opened, the two compounds are dispensed onto the dog by squeezing or collapsing the container or containers, either simultaneously or sequentially.

In a preferred embodiment of the invention, the composition comprising the combination as defined herein is packaged in a single dose package. Single dose containers make storage and disposal more convenient for animal owners.

In one embodiment of the invention, the composition is packaged with instructions, advising to mix the insecticides. In other embodiments of the invention, the instructions will direct the user to mix the insecticides upon application. In one embodiment of the invention, a container is provided with multiple single dose packages therein.

Accordingly, the present invention provides a kit suitable for implementing a method for controlling the spread of dirofilariosis, such as for example heartworm disease as defined herein. Said kit comprises one or several containers, wherein said containers comprise a combination of a neonicotinoid compound and a pyrethroid compound, and optionally IGR, as defined above, and preferably a leaflet giving instructions for administering said combination to a non-human animal infested with filarioid nematodes, such as *Dirofilaria* spp, or susceptible to have been infested with filarioid nematodes, such as *Dirofilaria* spp. According to a specific embodiment, the kit may comprise further containers comprising at least one macrocyclic lactone, and optionally further instructions for administering said macrocyclic lactone.

A product which can be used according to the method of the invention may more particularly be the product comprising dinotefuran-permethrin-pyriproxyfen, such as the one sold under the tradename Vectra®3D by Ceva Animal Health.

The examples below illustrate the present invention and are given as non-limiting illustrations.

EXAMPLES

Example 1: Anti-Feeding Repellency and Insecticidal Efficacy of a Topical Administration of the Combination of a Neonicotinoid Compound (Dinotefuran) and a Pyrethroid Compound (Permethrin) in Dogs Weekly Infested by Mosquitoes for One Month In a blinded, unicentre and controlled trial performed according to Good Clinical Practice, twelve dogs were randomly allocated to two groups of 6 dogs based on pre-treatment mosquito counts. Treatment was administered on day 0 with a topical combination for a minimal dose of 46.6 mg/kg permethrin, 6.40 mg/kg dinotefuran and 0.57 mg/kg pyriproxiyfen. Each dog was infested under sedation with 100 adult unfed female *Aedes aegypti* on days −6, 1, 7, 14, 21, and 28 after treatment. The whole body of dogs were exposed to mosquitoes. After 1 hour of exposure, mosquitoes were counted and classified as dead or alive and fed or unfed. The anti-feeding repellency effect of the product ranged from 87.0 and 94.7%. Insecticidal effect was above 93% until day 28. The combination was effective to kill mosquitoes, prevent blood-feeding by mosquitoes and was well tolerated by the treated dogs.

Example 2: Inhibition of the Transmission of *Dirofilaria immitis* Microfilariae to Mosquitoes by Weekly Exposure of Microfilaremic Dogs Treated Topically with a Neonicotinoid Compound (Dinotefuran), a Pyrethroid Compound (Permethrin) and an IGR Compound (Pyriroxyfen)

In a blinded, unicentre and controlled trial performed according to Good Clinical Practice, six dogs positive to heartworm (*Dirofilaria immitis*) and microfilaremic were randomly allocated to two groups of 3 dogs based on microfilaremia. Treatment was administered on day 0 with a topical combination for a minimal dose of 46.6 mg/kg permethrin, 6.40 mg/kg dinotefuran and 0.57 mg/kg pyriproxyfen. Each dog was infested under sedation with 100 adult unfed female *Aedes aegypti* on days -7, 7, 14, 21, and 28 after treatment. The whole body of dogs were exposed to mosquitoes. Immediately upon feeding, 20 engorged mosquitoes were collected from the cage by aspiration and cooled for 2 min prior to dissection. The midgut of each mosquito was stained and assessed under microscope for microfilaria count. The combination was well tolerated by the treated dogs. Before treatment, microfilaria counts of dogs were 400-32,100 microfilaria/mL and 95% of engorged mosquitoes had microfilaria (1-742). From day 7 to 28, none of the mosquitoes exposed to the treated dogs after treatment had microfilaria. The anti-uptake efficacy was 100% for 28 days after treatment. The combination was highly effective in inhibiting the uptake of microfilaria by mosquitoes from microfilaremic dogs for 1 month.

Example 3: Inhibition of the Development of *Dirofilaria immitis* 13 in Mosquitoes at the End of 16-Day Incubation Period after Each Weekly Exposure of Microfilaremic Dogs Treated Topically with a Neonicotinoid Compound (Dinotefuran), a Pyrethroid Compound (Permethrin) and an IGR Compound (Pyriroxyfen)

In a blinded, unicentre and controlled trial performed according to Good Clinical Practice, six dogs positive to heartworm (*Dirofilaria immitis*) and microfilaremic were randomly allocated to two groups of 3 dogs based on microfilaremia. Treatment was administered on day 0 with a topical combination for a minimal dose of 46.6 mg/kg permethrin, 6.40 mg/kg dinotefuran and 0.57 mg/kg pyriproxyfen. Each dog was infested under sedation with 100 adult unfed female *Aedes aegypti* on days -7, 7, 14, 21, and 28 after treatment. The whole body of dogs were exposed to mosquitoes. After 1 hour of exposure, mosquitoes were collected from the cage by aspiration and classified as live or dead, fed or unfed. The live mosquitoes were incubated and their survival was assessed daily for up to 16 days after feeding. The mosquitoes were dissected for the third larval stage of *D. immitis* (L3) counts. Of the cumulative total of 27 mosquitoes that fed on treated dogs during the 4 exposures, all were dead within 72 hours and no infective stage L3 was able to develop. Of the 60 engorged mosquitoes that fed on the control dogs and survived the 16-day incubation period, 55 (91.7%) had an average of 10.9 L3 (range, 1-39). The combination was highly effective in inhibiting the development of L3 in mosquitoes exposed to microfilaremic dogs for 1 month. The combination was proven effective to prevent the spreading of dirofilariosis from infected dogs. The combination was well tolerated by the treated dogs.

Example 4: Inhibition of the Transmission of a Resistant Strain of *Dirofilaria immitis* to Dogs Weekly Exposed for 1 Month to Infected Mosquitoes by Concomitant Treatment with a Macrocyclic Lactone and a Topical Combination of Neonicotinoid Compound (Dinotefuran) and Pyrethroid Compound (Permethrin)

In a blinded, unicentre and controlled trial performed according to Good Clinical Practice, thirty two dogs were randomly allocated to two groups of 8 dogs based on pre-treatment mosquito counts. In Group 1, no treatment was administered. In Group 2, treatment was administered on day 0 with a topical combination for a minimal dose of 46.6 mg/kg BW permethrin, 6.40 mg/kg BW dinotefuran and 0.57 mg/kg BW pyriproxyfen. In Group 3, treatment was administered on day 0 and 30 with an oral dose of milbemycin oxime (0.5 mg/kg BW). In Group 4, dogs were administered an oral dose of milbemycin oxime (0.5 mg/kg BW) on days 0 and 30 and a topical combination for a minimal dose of 46.6 mg/kg BW permethrin, 6.40 mg/kg BW dinotefuran and 0.57 mg/kg BW pyriproxyfen on day 0. Each dog was infested under sedation with 20 live adult unfed female *Culex pipiens* on days -6, 1, 7, 14, 21, and 28 after treatment. The whole body of dogs were exposed to mosquitoes. Starting from day 1, the mosquitoes were previously infected by blood-feeding on *Dirofilaria immitis* infected blood through a membrane and incubated for 16 days prior to the exposure. The strain of *D immitis* (JYD-34) was proven to be resistant to macrocyclic lactones, including milbemycin oxime. The number of *D immitis* L3 was assessed in a pool of mosquitoes to evaluate the challenge. After 1 hour of exposure, mosquitoes were counted and classified as fed or unfed. The development of *D immitis* was assessed by necropsy of the animals 6 months after treatment for adult worms counts. The anti-feeding repellency effect of the product ranged from 99.0 and 100%. There were in average 24.6 worms per dog in untreated Group 1 and 7.2 worms per dog in treated Group 3 with the macrocyclic lactone alone (efficacy 70.7%). Only one worm was found from one of the dogs in Group 2 treated with the topical combination (efficacy 99.5%). No worm was found in the dogs from Group 4 (efficacy 100%). The products were well tolerated by the dogs and the topical combination was shown to restaure at its highest level the efficacy of milbemycin oxime against a resistant strain of *D. immitis*. The combination of a neonicotinoid (dinotefuran) and a pyrethroid (permethrin) was demonstrated to contribute significantly to the prevention of the infection of dogs by heartworm.

The invention claimed is:
1. A method for controlling the spread of dirofilariosis to a non-infested dog from at least one of a strain of *D. immitis* resistant to macrocyclic lactones and having microfilaria that circulate in the bloodstream, comprising administering to the at least one infested dog, an effective dose of a combination of a neonicotinoid compound, a pyrethroid compound, wherein the macrocyclic lactone is milbemycin oxime, wherein the weight ratio of pyrethroid compound to neonicotinoid compound ranges from 4-15.

2. The method according to claim 1, wherein the neonicotinoid compound is dinotefuran.

3. The method according to claim 1, wherein the pyrethroid compound is permethrin.

4. The method according to claim 1, wherein the at least one infested dog is a dog diagnosed as infected with filarioid nematodes.

5. The method according to claim 1, wherein the combination further comprises an insect growth regulator (IGR).

6. The method according to claim 5, wherein the weight ratio of IGR to neonicotinoid compound ranges from 0.05-0.12.

7. The method according to claim 5, wherein the combination comprises permethrin in a concentration range of about 60 to 95%, dinotefuran in a concentration range of about 6 to 22%, and pyriproxyfen in a concentration range of about 0.8 to 4%.

8. The method according to claim 5, wherein the combination comprises permethrin in a concentration range of about 70 to 90%, dinotefuran in a concentration range of about 8 to 15%, and pyriproxyfen in a concentration range of about 0.9 to 1.5%.

9. The method according to claim 1, wherein the combination is applied topically to the skin or fur of the infested dog.

10. The method according to claim 1, wherein the at least one infested dog lives among a group of dogs.

11. The method according to claim 1, wherein filarioid nematodes are *Dirofilaria* spp.

12. The method according to claim 1, wherein the weight ratio of pyrethroid compound to neonicotinoid compound ranges from 6 to 9.

13. The method according to claim 1, wherein the weight ratio of pyrethroid compound to neonicotinoid compound ranges from 7-8.

14. The method according to claim 5, wherein the insect growth regulator (IGR) is selected in the group consisting of methoprene and pyriproxyfen.

15. The method according to claim 5, wherein the weight ratio of IGR to neonicotinoid compound ranges from 0.06 to 0.1.

16. The method according to claim 5, wherein the weight ratio of IGR to neonicotinoid compound ranges from 0.07-0.09.

* * * * *

UNITED STATES PATENT AND TRADEMARK OFFICE
CERTIFICATE OF CORRECTION

PATENT NO. : 10,952,988 B2
APPLICATION NO. : 15/743179
DATED : March 23, 2021
INVENTOR(S) : Marie Varloud et al.

Page 1 of 1

It is certified that error appears in the above-identified patent and that said Letters Patent is hereby corrected as shown below:

On the Title Page

Item (30), Foreign Application Priority Data:
"Jul. 10, 2015 (EP) .................................15306145"
Should be replaced to read:
--Jul. 10, 2015 (EP) .................................15306145.2--

In the Claims

In Claim 1, at Column 12, Line 60:
"a non-infested dog from at least one of a strain of *D. immitis*"
Should be replaced to read:
--a non-infested dog from at least one dog infested with filarioid nematodes of a strain of *D. immitis*--

In Claim 1, at Column 12, Lines 64-65:
"compound, wherein the macrocyclic lactone is milbemycin"
Should be replaced to read:
--compound, and a macrocyclic lactone, wherein the macrocyclic lactone is milbemycin--

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*